United States Patent [19]

Bleeker et al.

[11] Patent Number: 5,723,572

[45] Date of Patent: Mar. 3, 1998

[54] PROCESS FOR THE PREPARATION OF A LINEAR ALTERNATING COPOLYMER OF CARBON MONOXIDE WITH ETHENE AND ANOTHER OLEFINICALLY UNSATURATED COMPOUND

[75] Inventors: Erwin Paulus Petrus Bleeker; Johannes Adrianus Maria Van Broekhoven; Maria Barbara Hendrica Crijnen-Beers Van, all of Amsterdam, Netherlands

[73] Assignee: Shell Oil Company, Houston, Tex.

[21] Appl. No.: 663,467

[22] Filed: Jun. 17, 1996

[30] Foreign Application Priority Data

Jun. 12, 1995 [EP] European Pat. Off. ............ 95201313

[51] Int. Cl.$^6$ .................................................. C08G 67/02
[52] U.S. Cl. .................... 528/392; 528/222; 528/223; 528/224; 528/225; 524/706; 524/709; 524/710; 524/711; 524/730; 524/755; 524/779; 524/785; 524/846
[58] Field of Search .................... 528/222, 223, 528/224, 225, 392; 524/706, 709, 710, 711, 730, 755, 779, 785, 846

[56] References Cited

FOREIGN PATENT DOCUMENTS 88202658  11/1988  European Pat. Off. .

*Primary Examiner*—Samuel A. Acquah

[57] ABSTRACT

A process for the preparation of a linear alternating copolymer of carbon monoxide with ethene and another olefinically unsaturated compound (A) wherein a copolymer of which the molar ratio ($r_1$) of the monomer units originating in the olefinically unsaturated compound A to the monomer units originating in ethene is in the range of from 1:100 to 1:3, is prepared by contacting the monomers in the presence of a liquid diluent with a catalyst composition which is based on (a) a source of a Group VIII metal, and
(b) a bidentate ligand of the general formula $R^1R^2M^1$—R—$M^2R^3R^4$ (I) wherein $M^1$ and $M^2$ independently represent a phosphorus, arsenic or antimony atom, $R^1$, $R^2$, $R^3$ and $R^4$ independently represent unsubstituted or substituted hydrocarbyl groups and R represents a bivalent bridging group which consists of three atoms in the bridge of which the middle atom is a carbon or silicon atom which carries two monovalent substituents $R^5$ and $R^6$ consisting of carbon, hydrogen and optionally oxygen, and the two outer bridging atoms are carbon atoms, while the quotient $r_2/r_1$ is less than 24, in which quotient $r_1$ is as defined herein and $r_2$ is the molar ratio of the olefinically unsaturated compound A to ethene in the liquid phase.

18 Claims, No Drawings

PROCESS FOR THE PREPARATION OF A LINEAR ALTERNATING COPOLYMER OF CARBON MONOXIDE WITH ETHENE AND ANOTHER OLEFINICALLY UNSATURATED COMPOUND

FIELD

The present invention relates to a process for the preparation of a linear alternating copolymer of carbon monoxide with ethene and another olefinically unsaturated compound.

BACKGROUND

EP-A-257663 proposes the preparation of linear alternating copolymers of carbon monoxide with ethene and another olefinically unsaturated compound (A) can be by contacting the monomers with a catalyst composition which is based on (a) a source of a Group VIII metal, and (b) a bidentate ligand of the general formula $R^1R^2M^1$—Q—$M^2R^3R^4$ wherein $M^1$ and $M^2$ independently represent a phosphorus, arsenic or antimony atom, $R^1$, $R^2$, $R^3$ and $R^4$ independently represent unsubstituted or substituted hydrocarbyl groups and Q represents a bivalent bridging group which contains at least two carbon atoms in the bridge. The copolymers obtained are strictly alternating or, in other words, the monomer units originating in carbon monoxide and the monomer units originating in ethene and the olefinically unsaturated compound A occur in a strictly alternating order. The polymer chains consist of randomly arranged units —CO—($CH_2CH_2$)— and —CO—A'—, wherein A' denotes a monomer unit originating in the olefinically unsaturated compound A. A preferred bidentate ligand for use in this process is 1,3-bis[bis(2-methoxy-phenyl)phosphino]propane.

Using this process semi-crystalline copolymers can be prepared which can have a variety of melting points, depending on the quantity of the olefinically unsaturated compound A incorporated therein relative to the quantity of ethene. That is to say, starting from a copolymer of carbon monoxide and exclusively ethene the melting point thereof can be lowered by replacing monomer units originating in ethene by monomer units originating in the olefinically unsaturated compound A. Lowering the melting point favours a smooth melt processing of the copolymer.

However, a problem associated with this process is that a large excess of the olefinically unsaturated compound A needs to be present in the polymerization mixture to achieve an appreciable level of incorporation thereof. For example, a terpolymer of carbon monoxide, ethene and propene containing monomer units originating in propene in a quantity of about 6 mole-%, relative to the total of monomer units originating in ethene and propene, may be prepared in a slurry process in which the quantity of propene is as high as 50%-vol of the total liquid phase. This is disadvantageous, because the presence of a large excess of the olefinically unsaturated compound A reduces the capacity of the reactor employed for the copolymerization and recycling the excess involves the handling of an undesirable large quantity of material.

Previous attempts at improving this situation have involved variations in a number of process parameters such as the polymerization temperature, the ratio of carbon monoxide to the total of the olefins present and the relative quantities of catalyst components. However, these variations did not bring about a reduction in the quantity of the olefinically unsaturated compound A needed to achieve the desired level of incorporation. In some cases the variations resulted in an unacceptable decrease of the polymerization rate or of the molecular weight of the copolymer.

Surprisingly, it has now found that the use of a bidentate ligand which contains a particular bridging group connecting the atoms $M^1$ and $M^2$ provides a solution of the problem described above. The bridging group in question has three atoms in the bridge of which the middle atom carries two substituents which consist of carbon, hydrogen and optionally oxygen. A further decrease of the quantity of the olefinically unsaturated compound A present in the reaction mixture could now be achieved, substantially without detriment to the rate of polymerization, by increasing the molar ratio of carbon monoxide to the total of the olefins present in the polymerization mixture. By doing so even a copolymer with increased molecular weight could be obtained.

SUMMARY OF THE INVENTION

The invention is to a process for the preparation of a linear alternating copolymer of carbon monoxide with ethene and another olefinically unsaturated compound (A) wherein a copolymer of which the molar ratio ($r_1$) of the monomer units originating in the olefinically unsaturated compound A to the monomer units originating in ethene is in the range of from 1:100 to 1:3, is prepared by contacting the monomers in the presence of a liquid diluent with a catalyst composition which is based on (a) a source of a Group VIII metal, and (b) a bidentate ligand of the general formula $R^1R^2M^1$—R—$M^2R^3R^4$ (I) wherein $M^1$ and $M^2$ independently represent a phosphorus, arsenic or antimony atom, $R^1$, $R^2$, $R^3$ and $R^4$ independently represent unsubstituted or substituted hydrocarbyl groups and R represents a bivalent bridging group which consists of three atoms in the bridge of which the middle atom is a carbon or silicon atom which carries two monovalent substituents $R^5$ and $R^6$ consisting of carbon, hydrogen and optionally oxygen, and the two outer bridging atoms are carbon atoms, while the quotient $r_2/r_1$ is less than 24, in which quotient $r_1$ is as defined herein and $r_2$ is the molar ratio of the olefinically unsaturated compound A to ethene in the liquid phase.

The invention further relates to a process for the preparation of a linear alternating copolymer of carbon monoxide with ethene and another olefinically unsaturated compound (A) wherein a copolymer of which the molar ratio (r1) of the monomer units originating in the olefinically unsaturated compound A to the monomer units originating in ethene is in the range of from 1:100 to 1:3, is prepared by contacting the monomers with a catalyst composition which is based on (a) a source of a Group VIII metal, and (b) a bidentate ligand of the general formula (I) with $M^1$, $M^2$, $R^1$, $R^2$, $R^3$, $R^4$ and R as defined herein before, while the quotient $r_2/r_3$ is less than 0.9, in which quotient $r_2$ is the molar ratio of the olefinically unsaturated compound A to ethene in the reaction phase, and $r_3$ is the molar ratio of the olefinically unsaturated compound A to ethene in the reaction phase of an identical process which is carried out to obtain a copolymer having the same ratio $r_1$ as the copolymer to be prepared except that in the latter process the bidentate ligand of the general formula (I) is replaced by an equimolar quantity of a bidentate ligand of the general formula $R^1R^2M$—$CH_2$—$CH_2$—$CH_2$—$M^2R^3R^4$ wherein the groups $M^1$, $M^2$, $R^1$, $R^2$, $R^3$ and $R^4$ are chosen as for the bidentate ligand of the formula (I) and that $r_3$ is not equal to $r_2$ at equal total molar quantities of the olefinically unsaturated compound A and ethene.

In addition the invention relates to a further process for the preparation of a linear alternating copolymer of carbon monoxide with an olefinically unsaturated compound (A), not being ethene, and optionally ethene comprising contacting carbon monoxide with the olefinically unsaturated compound A and optionally ethene in the presence of a suitable catalyst, on the understanding that at least a part of the olefinically unsaturated compound A has been recovered from a preceding process for the preparation of a linear alternating copolymer of carbon monoxide with ethene and the olefinically unsaturated compound A which preceding process comprises contacting the monomers with a catalyst composition which is based on (a) a source of a Group VIII metal, and (b) a bidentate ligand of the general formula (I) with $M^1$, $M^2$, $R^1$, $R^2$, $R^3$, $R^4$ and R as defined herein.

DETAILED DESCRIPTION

The preceding and the further process may represent consecutive phases of the same continuous process in which a recycle of the olefinically unsaturated compound A is applied. For a wide range of olefinically unsaturated compounds A (i.e. independent of their structure and their molecular weight) it holds that the copolymers having a molar ratio $r_1$ from 1:100 to 1:3 have a melting point in the range of from about 150° C. to about 245° C. This is particularly the case for aliphatic a-olefins consisting of carbon and hydrogen, typically having up to 10 carbon atoms, more typically up to 6 carbon atoms. It is preferred that copolymers are prepared in which the molar ratio r is in the range of from 1:50 to 1:5. These copolymers have a melting point in the range of from about 180° C. to about 240° C. In view of an advantageous balance of mechanical properties of the copolymers and their melt processing temperature it is preferred to prepare copolymers which have a molar ratio $r_1$ in the range of from 1:25 to 1:10, corresponding with a melting point in the range of from about 210° to about 235° C. Another preferred category of copolymers have the molar ratio $r_1$ in the range of from 1:10 to 1:5, corresponding with a melting point in the range of from about 180° to about 210° C.

In the present specification and claims the term "Group VIII metal" encompasses the noble metals ruthenium, rhodium, palladium, osmium, iridium and platinum, and the iron group metals iron, cobalt and nickel.

The catalyst composition suitable for use in the process of the invention is based on a source of cations of the metal. Suitable sources of cations of metals of Group VIII include salts of mineral acids, such as salts of sulphuric acid, nitric acid and phosphoric acid, and salts of sulphonic acids, such as methanesulphonic acid and para-toluenesulphonic acid. Preferred sources are salts of carboxylic acids, in particular those having up to 6 carbon atoms, such as acetic acid, propionic acid and trifluoroacetic acid. Metals in their elemental form, or in a zero-valent state thereof may be used as the action source. For example, they may be in complex form, such as complexes wherein the Group VIII metal is covalently bonded to one or two hydrocarbyl groups.

Catalyst compositions based on a noble Group VIII metal are preferred, those based on palladium being most preferred. A preferred source of palladium is palladium (11) acetate.

The catalyst composition of the invented process is further based on a bidentate ligand of the general formula $$R^1R^2M^1—R—M^2R^3R^4 \quad (I)$$

with $M^1$, $M^2$, $R^1$, $R^2$, $R^3$, $R^4$ and R as defined herein.

In the ligands of formula (I) $M^1$ and $M^2$ preferably represent phosphorus atoms. $R^1$, $R^2$, $R^3$ and $R^4$ may independently represent optionally polar substituted alkyl, aryl, alkaryl, aralkyl or cycloalkyl groups.

It is preferred that at least one of $R^1$, $R^2$, $R^3$ and $R^4$ represents an aryl group which is polar substituted. Suitable polar groups include halogen atoms, such as fluorine and chlorine, alkoxy groups such as methoxy and ethoxy groups and alkylamino groups such as methylamino-, dimethylamino- and diethylamino groups. Alkoxy groups and alkylamino groups contain in particular up to 5 carbon atoms in each of their alkyl groups.

It is preferred that each of $R^1$, $R^2$, $R^3$ and $R^4$ represents an aryl group, typically a phenyl group, substituted in particular at an ortho position with respect to $M^1$ or $M^2$, with a polar group, especially an alkoxy group, more especially a methoxy group.

In the ligands of formula (I), R represents a bridging group which consists of three atoms in the bridge of which the middle atom is a carbon or silicon atom which carries two substituents $R^5$ and $R^6$ which consist of carbon, hydrogen and optionally oxygen, and the two outer bridging atoms are carbon atoms, typically the carbon atoms of methylene groups ($—CH_2—$).

The substituents $R^5$ and $R^6$ are typically identical to one another. They may be, for example, aliphatic or aromatic hydrocarbyl groups and they may contain ether linkages, such as in alkoxyalkyl groups. They have typically up to 15 carbon atoms, more typically up to 10 carbon atoms. The substituents $R^5$ and $R^6$ may suitably be connected to one another by an additional link, i.e. other than by the middle atom of the bridge, so that they form together with that middle atom a ring structure. For example, such a situation represents itself when the substituents together form a $—CH_2—CH_2—CH_2—CH_2—$ group or a $—CH_2—O—C(CH_3)_2—O—CH_2—$ group. The substituents $R^5$ and $R^6$ are preferably alkyl groups, in particular methyl groups.

Preferred ligands are 2,2-dimethyl-1,3-bis(2-methoxyphenyl,phenyl-phosphino)propane, 2,2-dimethyl-1,3-bis[bis(2-methoxyphenyl)-phosphino]propane and 2,2-dimethyl-1,3-bis[bis(2-methoxyphenyl)-phosphino]-2-silapropane. The ligands mentioned here are known from EP-A-300583 and EP-A-296687.

The amount of bidentate ligand supplied may vary considerably, but is usually dependent on the amount of metal of Group VIII, present in the catalyst composition. Preferred amounts of bidentate ligands are in the range of 0.5 to 8, preferably in the range of 0.5 to 2 moles per gram atom of metal of Group VIII.

The catalyst system may be based on an additional component which functions during the copolymerization as a source of anions which are non- or weakly co-ordinating with the Group VIII metal. Additional components applicable as a source of anions are, for example, protic acids, salts of protic acids, Lewis acids, combinations of Lewis acids and protic acids, and salts derivable from such combinations. Anions of strong acids are preferred, particularly acids having a pKa of less than 6, and more preferably less than 4. It is most preferred that they have a pKa of less than 2, when measured in aqueous solution at 18° C. Examples of suitable strong acids are the above mentioned acids which may also participate in the Group VIII metal salts, e.g. trifluoroacetic acid. Other suitable strong acids are adducts of boric acid and 1,2-diols, catechols or salicylic acids. Salts of these acids may be used as well. Other suitable salts contain one or more hydrocarbylborate anions or carborate anions, such as sodium tetrakis[bis-3,5-(trifluoromethyl) phenyl]borate, lithium tetrakis(perfluorophenyl)borate and cobalt carborate ($CO(B_{11}CH_{12})_2$). Suitable Lewis acids are, for example, $BF_3$, $SnCl_2$, $SnF_2$ and $Sn(CF_3SO_3)_2$, and hydrocarbylboranes, such as triphenylborane, tris (perfluorophenyl)-borane and tris[bis-3,5-(trifluoromethyl) phenyl]borane. Protic acids with which Lewis acids may be combined are for example sulphonic acids and hydrohalogenic acids, in particular HF. An example of a combination of a Lewis acid with a protic acid is tetrafluoboric acid ($HBF_4$). Other compounds which may be mentioned in this context are aluminoxanes, in particular methyl aluminoxanes and t-butyl aluminoxanes.

The amount of the additional component which functions as an anion source is preferably selected in the range of from 0.5–50 equivalents per gram atom of Group VIII metal. Preferably, the amount is in the range of 1–25 equivalents per gram atom of Group VIII metal. However, aluminoxanes are typically used in such a quantity that the molar ratio of aluminium to the Group VIII metal is in the range of from 4000:1 to 10:1, preferably from 2000:1 to 100:1, and more preferably from 500:1 to 200:1.

The performance of the catalyst composition may be improved by incorporating therein an organic oxidant promoter, such as a quinone. Preferred promoters are selected from the group consisting of benzoquinone, naphthoquinone and anthraquinone. The amount of promoter is advantageously in the range of from 1 to 50, preferably in the range of from 1 to 10 mole per gram atom of metal of Group VIII.

The amount of catalyst used in the process of the invention may vary between wide limits. It is advantageous to employ the smallest quantity of catalyst composition possible in relation to the quantity of copolymer to be prepared. Recommended quantities of catalyst composition are in the range of $10^{-8}$ to $10^{-2}$, calculated as gram atoms of metal of Group VIII per mole of olefinically unsaturated compound to be copolymerized with carbon monoxide. Preferred quantities are in the range of $10^{-7}$ to $10^{-3}$ on the same basis.

The olefinically unsaturated compounds A include compounds consisting exclusively of carbon and hydrogen and compounds which additionally comprise hetero atoms, such as unsaturated esters. The olefinically unsaturated compounds A comprise typically up to 10 carbon atoms, more typically up to 6 carbon atoms. Unsaturated hydrocarbons are preferred. Examples of suitable monomers are aliphatic a-olefins such as propene and butene-1, cyclic olefins such as cyclopentene and dicyclopentadiene, aromatic olefins such as styrene and alpha-methyl-styrene, and vinyl esters such as vinyl acetate and vinyl propionate. Preferably, carbon monoxide is copolymerized with ethene and another a-olefin, in particular propene or butene-1.

The molar ratio of the olefinically unsaturated compounds present in the reaction phase is determined by the molar ratio at which they are to be incorporated into the copolymer. In accordance with this invention, the molar ratio of the olefinically unsaturated compounds present in the reaction phase is governed by the quotient $r_2/r_1$ or by the quotient $r_2/r_3$, which are both as defined herein. The quotient $r_2/r_1$ is less than 24. Typically the quotient $r_2/r_1$ is at least 5; preferably the quotient $r_2/r_1$ is in the range of from 10 to 22. The quotient $r_2/r_3$ is less than 0.9. However, it is preferred that the quotient $r_2/r_3$ is in the range of from 0.2 to 0.85, more preferably in the range of from 0.4 to 0.8. When more than one olefinically unsaturated compound A is employed different ratios $r_1$, $r_2$ and $r_3$ apply separately to each of them.

Generally, the molar ratio of carbon monoxide to olefinically unsaturated compounds may vary between wide ranges. It has been found that the quantity of the olefinically unsaturated compound present in the reaction phase can be reduced, substantially without serious detriment to the polymerization rate by increasing in the reaction phase the molar ratio of carbon monoxide to the total of ethene and the olefinically unsaturated compound A. Indeed, it can even have an enhancing effect on the polymer's molecular weight. Preferably this molar ratio is more than 0.1:1. However, it is preferred that it not exceed 0.45:1. Good results can also be obtained, particularly with respect to the molecular weight of the copolymers, when in the reaction phase the molar ratio of carbon monoxide to the total of ethene and the olefinically unsaturated compound A is in the range of from 0.12:1 to 0.3:1.

The copolymerization process of this invention is typically carried out in the presence of a liquid diluent, in which case the liquid phase is the reaction phase of the polymerization mixture. Preferably a diluent is used in which the copolymer to be prepared forms a suspension, in view of which a diluent may be selected in which the copolymer is insoluble or virtually insoluble. Examples of liquid diluents are ketones (e.g. acetone), chlorinated hydrocarbons (e.g. chloroform or dichloromethane), aromatics (e.g. toluene, benzene, chlorobenzene) and protic diluents, such as the lower alcohols (e.g. methanol and ethanol). Mixtures of liquid diluents may be used as well, for example protic diluents may comprise aprotic compounds. In some embodiments, the process of this invention may also be carried out as a gas phase process, in which case the gas phase is the reaction phase of the polymerization mixture.

When the process of this invention is carried out such that the prepared copolymer is formed as a suspension in a liquid diluent it is advantageous to have a solid particulate material suspended in the diluent before the monomers are contacted with the catalyst composition. Typically a copolymer of carbon monoxide and an olefinically unsaturated compound is used as the solid particulate material. It particularly preferred that the solid is a copolymer which is based on the same monomers as the copolymer to be prepared. The latter means that, for example, when a linear alternating copolymer of carbon monoxide, ethene and propene will be prepared a linear alternating copolymer of carbon monoxide, ethene and propene from an earlier polymer preparation will be suspended in the diluent. Other suitable solid particulate materials may be inorganic or organic materials, such as silica, alumina, talc, soot and polymers, for example polyethene, polypropene and polystyrene. The solid particulate material is suitably used in a quantity of 0.1–20% w. relative to the weight of the diluent, more suitably in a quantity of 0.5–10% w. The bulk density of the solid particulate material is typically in the range of 50–1000 kg/m³, in particular in the range of 100–500 kg/m³. The solid particulate material has typically an average particle size of $10^{-6}$–$10^{-3}$ m, in particular $10^{-6}$–$5\times10^{-4}$ m. The average particle size is determined as follows. With the aid of a commercially available particle size analyser, a cumulative weight distribution of a representative sample of the solid particulate material is determined as a function of the particle size. The cumulative weight distribution function is converted into a cumulative surface area distribution function, as described by Terence Allen in Particle Size Measurement (Chapman and Hall, London, 1981), p. 122 ff. The average particle size is found as the median of the cumulative surface area distribution function.

The copolymerization process is usually carried out at a temperature in the range of 20° to 200° C., preferably at a temperature in the range of 30° to 150° C. The reaction is conveniently performed at a pressure in the range of 2 to 200 bar, pressures in the range of 20 to 100 bar being preferred. The process may be carried out as a batch process or as a continuous process. In the latter case it is advantageous to apply two or more reactors connected in series as this increases the quantity of polymer which can be prepared within a given period of time given a particular reaction volume and a particular quantity of catalyst.

The excess of the olefinically unsaturated compound A present in the reaction phase, and in the entire polymerization mixture, is particularly low in the process of this invention. This favours a smooth recycle of the olefinically unsaturated compound A. The recycle can be accomplished by using methods which are known and which can be selected according to the physical properties of the olefinically unsaturated compound A and those of other components present in the copolymerization mixture. The recycle may comprise the steps of recovering the olefinically unsaturated compound A by partly or completely separating it from other reaction components present and supplying it to a subsequent copolymerization process with addition of fresh olefinically unsaturated compound A. Optionally a bleed may be applied in order to avoid a build-up of impurities.

The copolymers can be recovered from the copolymerization process using known methods. They can suitably be used as thermoplastics for fibres, films or sheets, or for injection moulding, compression moulding and blowing applications. They may be used for applications in the automotive industry, for the manufacture of packaging materials for food and drinks and for various uses in the domestic sphere.

The invention will be illustrated by the following examples. The molar ratio of propene to ethene as incorporated in a copolymer was determined indirectly from the copolymer's melting point using a predetermined relation between the melting point and the said ratio. The melting points determined by differential scanning calorimetry, the ratios were determined by $^{13}$C-NMR spectroscopy. The limiting viscosity numbers (LVN) of a copolymer was used as a measure for its molecular weight: a higher LVN indicating a higher molecular weight. The LVN of a copolymer was determined from the inherent viscosity at 60° C. of four solutions of the copolymer in m-cresol with different copolymer concentrations.

EXAMPLE 1

A copolymer of carbon monoxide with ethene and propene was prepared as follows.

A 2-litre autoclave equipped with baffles and a mechanical stirrer was charged with 880 ml methanol and 15 g of a powder of a copolymer of carbon monoxide with ethene and propene obtained in a previous copolymerization. The autoclave was closed and purged with nitrogen to remove the air present. The contents of the autoclave were heated to 76° C. Carbon monoxide, ethene and propene were fed into the autoclave such that their partial pressures were 13 bar, 23 bar and 9 bar, respectively. In the liquid phase the molar ratio of propene to ethene was 1:1 and the molar ratio of carbon monoxide to the total of ethene and propene was 0.054:1. A catalyst solution comprising 20 ml acetone, 0.045 mmoles palladium acetate, 0.047 mmoles 2,2-dimethyl-1,3-bis[bis(2-methoxyphenyl)phosphino]-2-silapropane, and 0.9 mmoles trifluoroacetic acid was injected into the autoclave. The pressure of the autoclave was maintained by supplying a mixture of carbon monoxide and ethene (1:1 molar ratio). After 6 hours the pressure was released and the autoclave was allowed to cool to room temperature. The polymer product was recovered by filtration, washed with methanol and dried.

The average polymerization rate was calculated from the yield of copolymer. The results are shown in Table 1.

EXAMPLES 2–5

A copolymer of carbon monoxide with ethene and propene was prepared as indicated in Example 1, except that the partial pressures of carbon monoxide, ethene and propene were altered as shown in Table 1.

The molar ratios of the monomers in the liquid phase and the results are indicated in Table 1.

TABLE 1

| Example | 1 | 2 | 3 | 4 | 5 |
|---|---|---|---|---|---|
| Partial pressures (bar) | | | | | |
| carbon monoxide (CO) | 13 | 23 | 30 | 33 | 13 |
| ethene (C2) | 23 | 16 | 12 | 9 | 19 |
| propene (C3) | 9 | 7 | 5 | 4 | 14 |
| Molar ratio in the liquid phase | | | | | |
| C3/C2 ($r_2$) | 1.0 | 1.1 | 1.1 | 1.1 | 1.8 |
| CO/(C2 + C3) | 0.054 | 0.14 | 0.26 | 0.38 | 0.057 |
| Polymerization rate (kg/(g Pd. hour)) | 10 | 8.4 | 9.0 | 6.2 | 9.6 |
| Copolymer product | | | | | |
| molar ratio C3/C2 ($r_1$) | 0.058 | 0.053 | 0.058 | 0.064 | 0.14 |
| LVN (dl/g) | 1.6 | 1.9 | 1.9 | 1.5 | 1.0 |
| Quotient $r_2/r_1$ | 17 | 21 | 19 | 17 | 13 |

EXAMPLE 6

A copolymer of carbon monoxide with ethene and propene was prepared as indicated in Example 5, except that 0.27 mmoles trifluoroacetic acid was used instead of 0.9 mmoles.

The polymerization rate was 7.7 kg/g palladium.hour). The molar ratio of propene to ethene in the copolymer obtained ($r_1$) was 0.14:1. Thus, the quotient $r_2/r_1$ amounted to 13. The LVN of the copolymer was 0.85 dl/g.

EXAMPLE 7

A copolymer of carbon monoxide with ethene and propene was prepared as indicated in Example 2, except that the polymerization temperature was 82° C. instead of 76° C. In the liquid phase the molar ratio of propene to ethene was 1.1:1 and the molar ratio of carbon monoxide to the total of ethene and propene was 0.15:1.

The polymerization rate was 15 kg/g palladium.hour). The molar ratio of propene to ethene in the copolymer obtained ($r_1$) was 0.058:1. Thus, the quotient $r_2/r_1$ amounted to 19. The LVN of the copolymer was 1.2 dl/g.

EXAMPLE 8 (Comparative)

A copolymer of carbon monoxide with ethene and propene was prepared as indicated in Example 1, except that 0.047 mmoles 1,3-bis[bis-(2-methoxyphenyl) phosphino] propane was used instead of 2,2-dimethyl-1,3-bis[bis(2-methoxyphenyl) phosphino]-2-silapropane.

The molar ratio of propene to ethene in the copolymer obtained ($r_1$) was 0.031:1. Thus, the quotient $r_2/r_1$ amounted to 32.

EXAMPLE 9 (Comparative)

A copolymer of carbon monoxide with ethene and propene was prepared as indicated in Example 1, except that 0.047 mmoles 1,3-bis[bis-(2-methoxyphenyl) phosphino] propane was used instead of 2,2-dimethyl-1,3-bis[bis(2-methoxyphenyl) phosphino]-2-silapropane, and that the partial pressures of carbon monoxide, ethene and propene were 23 bar, 34 bar and 23 bar, respectively. In the liquid phase the molar ratio of propene to ethene was 1.5:1 and the molar ratio of carbon monoxide to the total of ethene and propene was 0.055:1.

The molar ratio of propene to ethene in the copolymer obtained ($r_1$) was 0.058:1. Thus, the quotient $r_2/r_1$ amounted to 26.

When the results of examples 1–4 and 7 (according to the invention) are compared with those of comparative example 8 it can be seen that the use of 2,2-dimethyl-1,3-bis[bis(2-methoxyphenyl)phosphino]-2-silapropane as the bidentate ligand led to about 6%-mole incorporation of propene in the copolymer, relative to ethene, at a propene/ethene molar ratio in the liquid phase of about 1:1, while the incorporation was about 3%-mole when 1,3-bis[bis(2-methoxyphenyl) phosphino]propane was used at the same propene/ethene ratio in the liquid phase. A similar trend can be seen upon comparing examples 5 and 6 (according to the invention) with comparative example 9. The differences in the efficiencies of propene incorporation can also be seen by comparing the quotients $r_2/r_1$.

In examples 2 and 9 copolymers were prepared which have virtually the same quantities of propene incorporated. The reaction conditions differed in the molar ratios of propene to ethene and in that, as the ligand, 2,2-dimethyl-1,3-bis[bis(2-methoxyphenyl)phosphino]-2-silapropane was used in example 2 and 1,3-bis[bis(2-methoxyphenyl) phosphino]propane in example 9. Although the total molar quantities of propene and ethene were not equal in these examples, the quotient $r_2/r_3$ can be calculated to amount to 0.73. (It is noted that in examples 1–4, at a fixed value of $r_2$, variations in the total molar quantities of propene and ethene have not influenced the propene incorporation.)

A comparison of examples 2–4 with example 1 shows that the molar ratio of carbon monoxide to the total of ethene and propene can be increased without a substantial decrease of the polymerization rate. Especially attractive results, also with respect to the LVN of the copolymer, were accomplished in examples 2 and 3.

By comparing the partial pressures of propene in example 3 and example 9 it can be seen that for the preparation of copolymers with approximately the same content of monomer units originating in propene 4–5 times less propene may be present in the polymerization mixture when 2,2-dimethyl-1,3-bis[bis(2-methoxyphenyl)phosphino]-2-silapropane is used as the bidentate ligand instead of 1,3-bis[bis(2-methoxyphenyl)-phosphino]propane.

We claim as our invention:

1. A process for the preparation of a linear alternating copolymer of carbon monoxide with ethene and another olefinically unsaturated compound (A) wherein a copolymer of which the molar ratio ($r_1$) of the monomer units originating in the olefinically unsaturated compound A to the monomer units originating in ethene is between about 1:100 to 1:3, is prepared by contacting the monomers in the presence of a liquid diluent with a catalyst composition comprising:

(a) a source of a Group VIII metal, and
    (b) a bidentate ligand of the formula $R^1R^2M^1$—R—$M^2R^3R^4$ (I) wherein $M^1$ and $M^2$ independently represent a phosphorus, arsenic or antimony atom, $R^1$, $R^2$, $R^3$ and $R^4$ independently represent unsubstituted or substituted hydrocarbyl groups and R represents a bivalent bridging group which consists of three atoms in the bridge of which the middle atom is a carbon or silicon atom which carries two monovalent substituents $R^5$ and $R^6$ consisting of carbon, hydrogen and optionally oxygen, and the two outer bridging atoms are carbon atoms, wherein $r_2$ is the molar ratio of the olefinically unsaturated compound A to ethene in the liquid phase and the quotient $r_2/r_1$ is less than 24.

2. A process as claimed in claim 1, wherein the quotient $r2/r1$ is at least 5.

3. A process as claimed in claim 1 whereoin the quotient $r_2/r_1$ is in the between about 10 and 22.

4. A process for the preparation of a linear alternating copolymer of carbon monoxide with ethene and another olefinically unsaturated compound (A) wherein the molar ratio ($r_1$) of the monomer units originating in the olefinically unsaturated compound A to the monomer units originating in ethene is in the range of from 1:100 to 1:3, is prepared by contacting the monomers with a catalyst composition comprising:

(a) a source of a Group VIII metal, and
    (b) a bidentate ligand of the general formula $R^1R^2M^1$—R—$M^2R^3R^4$ (I) wherein $M^1$ and $M^2$ independently represent a phosphorus, arsenic or antimony atom, $R^1$, $R^2$, $R^3$ and $R^4$ independently represent unsubstituted or substituted hydrocarbyl groups and R represents a bivalent bridging group which consists of three atoms in the bridge of which the middle atom is a carbon or silicon atom which carries two monovalent substituents $R^5$ and $R^6$ consisting of carbon, hydrogen and optionally oxygen, and the two outer bridging atoms are carbon atoms, wherein the quotient $r_2/r_3$ is less than 0.9, in which quotient $r_2$ is the molar ratio of the olefinically unsaturated compound A to ethene in the reaction phase, and $r_3$ is the molar ratio of the olefinically unsaturated compound A to ethene in the reaction phase of an identical process which is carried out to obtain a copolymer having the same ratio $r_1$ as the copolymer to be prepared except that in the latter process the bidentate ligand of the general formula (I) is replaced by an equimolar quantity of a bidentate ligand of the general formula $R^1R^2M^1$—$CH_2$—$CH_2$—$CH_2$—$M^2R^3R^4$ wherein $r_3$ is not equal to $r_2$ at equal total molar quantities of the olefinically unsaturated compound A and ethene.

5. A process as claimed in claim 4, wherein the quotient $r_2/r_3$ is between about 0.2 and 0.85.

6. A process as claimed in claim 4 wherein the quotient $r_2/r_3$ is between about 0.4 and 0.8.

7. A process as claimed in claim 4 wherein a copolymer is prepared of which the molar ratio $r_1$ is in the range of from 1:25 to 1:10 or in the range of from 1:10 to 1:5.

8. A process as claimed in claim 1, wherein the Group VIII metal is palladium and $R^1$, $R^2$, $R^3$ and $R^4$ represent phenyl groups which are substituted at an ortho position with respect to $M^1$ or $M^2$, with an alkoxy group, the two outer bridging atoms of the bridging group R are the carbon atoms of methylene groups (—$CH_2$—), and the substituents $R^5$ and $R^6$ are alkyl groups.

9. A process as claimed in claim 1 wherein the bidentate ligand of formula (I) is selected from the group consisting of 2,2-dimethyl-1,3-bis(2-methoxyphenyl, phenylphosphino) propane, 2,2-dimethyl-1,3-bis[bis(2-methoxyphenyl) phosphino]propane and 2,2-dimethyl-1,3-bis[bis(2-methoxyphenyl) phosphino]-2-silapropane.

10. A process as claimed in claim 1 wherein the bidentate ligand of formula (I) is applied in a quantity of between about 0.5 and 2 moles per gram atom of metal of Group VIII.

11. A process as claimed in claim 1, wherein the catalyst composition further comprises a source of anions selected from the group consisting of protic acids, salts of protic acids, Lewis acids, combinations of Lewis acids and protic acids, salts derivable from such combinations, salts containing one or more hydrocarbylborate anions or carborate anions, and aluminoxanes.

12. A process as claimed in claim 11, wherein the source of anions is an acid having a pKa of less than 4 when measured in aqueous solution at 18° C.

13. A process as claimed in claim 11, wherein the amount of the additional component is between about 1 and 25 equivalents per gram atom of Group VIII metal.

14. A process as claimed in claim 13 wherein aluminoxane is used as an the component and the molar ratio of aluminium to the Group VIII metal is between about 2000:1 and 100:1.

15. A process as claimed in claim 1 wherein in a given phase, the molar ratio of carbon monoxide to the total of ethene and the olefinically unsaturated compound A is between about 0.1:1 about 0.45:1.

16. A process as claimed in claim 1 wherein the olefinically unsaturated compounds A is an a-olefin, the process is carried out in the presence of a liquid diluent as the reaction phase in which liquid diluent the prepared copolymer is formed as a suspension, it is carried out at a temperature between about 30° and 150° C. and at a pressure between about 20 and 100 bar using a quantity of catalyst composition in the range of $10^{-7}$ to $10^{-3}$, calculated as gram atoms of metal of Group VIII per mole of olefinically unsaturated compound to be copolymerized with carbon monoxide.

17. A process for the preparation of a linear alternating copolymer of carbon monoxide with an olefinically unsaturated compound (A), other than ethene, and optionally ethene comprising contacting carbon monoxide with the olefinically unsaturated compound A and optionally ethene in the presence of a suitable catalyst, wherein at least a part of the olefinically unsaturated compound A has been recovered from a preceding process for the preparation of a linear alternating copolymer of carbon monoxide with ethene and the olefinically unsaturated compound A which preceding process comprises contacting the monomers with a catalyst composition comprising:

(a) a source of a Group VIII metal, and (b) a bidentate ligand of the general formula $R^1R^2M^1$—R—$M^2R^3R^4$ (I) wherein $M^1$ and $M^2$ independently represent a phosphorus, arsenic or antimony atom, $R^1$, $R^2$, $R^3$ and $R^4$ independently represent unsubstituted or substituted hydrocarbyl groups and R represents a bivalent bridging group which consists of three atoms in the bridge of which the middle atom is a carbon or silicon atom which carries two monovalent substituents $R^5$ and $R^6$ consisting of carbon, hydrogen and optionally oxygen, and the two outer bridging atoms are carbon atoms.

18. A process as claimed in claim 17 carried out using ethene as one of the monomers.

* * * * *